United States Patent [19] [11] Patent Number: 5,518,656
Furuta et al. [45] Date of Patent: May 21, 1996

[54] FLUORESCENT DETECTING AGENTS

[75] Inventors: Yasusi Furuta, Arida; Yoshisada Tamura, Wakayama, both of Japan

[73] Assignee: Nippon Chemical Works Co., Ltd., Wakayama, Japan

[21] Appl. No.: 376,398

[22] Filed: Jan. 23, 1995

Related U.S. Application Data

[62] Division of Ser. No. 172,909, Dec. 27, 1993, abandoned.

[51] Int. Cl.⁶ .................................................. C09K 11/06
[52] U.S. Cl. .............................. 252/301.19; 427/8; 73/36
[58] Field of Search ........................... 252/301.19; 427/8; 73/36; 106/21 R, 21 A, 498

[56] References Cited

FOREIGN PATENT DOCUMENTS 1059687  2/1967  United Kingdom .

OTHER PUBLICATIONS

Chemical Abstract citation 120:206812w, Jun. 27, 1993, JP 05–160532.
Chemical Abstract citation 121:144998w, Jan. 11, 1994; JP 06/3291.

*Primary Examiner*—Melissa Bonner
*Attorney, Agent, or Firm*—Oblon, Spivak, McClelland, Maier & Neustadt

[57] ABSTRACT

A fluorescent detecting agent comprising a naphthalene compound of formula (I)

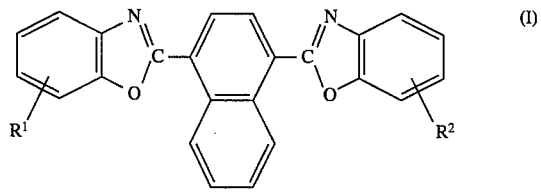

wherein $R^1$ and $R^2$ may be the same or different and each represents an alkyl group of 4 to 8 carbon atoms and/or a pyraxoline compound of formula (II)

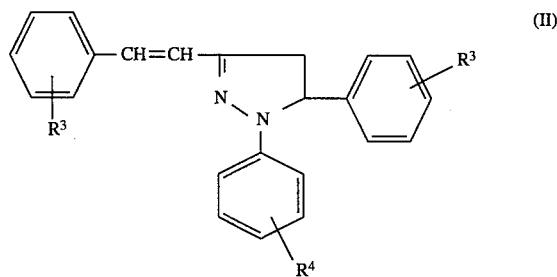

wherein $R^3$ and $R^4$ may be the same or different and each represents hydrogen, an alkoxy group of 1 to 8 carbon atoms or an alkyl group of 4 to 8 carbon atoms, provided that at least one of $R^3$ and $R^4$ represents an alkyl group of 4 to 8 carbon atoms. They are used for a visual inspection or an automatic optical inspection (AOI) and a fluorescent penetrant examination.

7 Claims, No Drawings

FLUORESCENT DETECTING AGENTS

This is a division of application Ser. No. 08/172,909 filed on Dec. 27, 1993, now abandoned.

FIELD OF THE INVENTION

This invention relates to fluorescent detecting agents comprising 1,4-dibenzoxazolylnaphthalene compounds and/or 1,5-diphenyl-3-styrylpyrazoline compounds, which are used for a visual inspection or an automatic optical inspection (AOI) and a fluroescent penetrant examination.

BACKGROUND OF THE INVENTION

The visual inspection or automatic optical inspection has been used for the inspection of coated state and uniform distribution in paints, inks, primers and adhesives and the inspection of applied pattern and finished circuit in the field of a photoresist. The penetrant examination has been applied to a non-destructive penetrant examination of fine defects in the surface of cast articles, machine parts and in the face of weld. A large number of dyes and fluorescent brighteners have been employed as fluorescent detecting agents for those inspections and examinations.

However, dyes and fluorescent brighteners mostly colored with pale yellow to yellow often give undesirable contamination to the material to be inspected. Further, the fluorescent brighteners cannot exhibit sufficient detection effect, since a wavelength of the fluorescent emission is too short. In addition to the above disadvantages of prior fluorescent detecting agents, problem remains that there are no materials satisfying the solubility in organic solvents, the compatibility with resin compositions and the stability of the dispersion when used in the form of fine particles, which are important properties indispensable to practical use. This provides an obstacle to a wide range of applications of fluorescent detecting agents.

For the penetrant examination, for instance, fluorescent detecting agents are used as a solution or dispersion in a penetrant. In the application of those agents to paints, inks, primers and adhesives, they are added in the form dissolved in a solvent or dispersed in fine particles.

In the preparation of a prepreg in the manufacture of a glass epoxy laminate in the field of photoresist, for instance, fluorescent detecting agents are used in the form of fine dispersion or solution together with an ultraviolet light screening material to coat or impregnate in a silane treated glass cloth or nonwoven fabric or they are used in the form dissolved in a resin composition constituting a laminated (epoxy varnish, etc.). When they are used as a fine dispersion, the stability, especially re-cohesiveness of finely divided particles is an important factor in practical use. When they are used as a solution, the solubility and stability in an organic solvent and epoxy varnish are an important factor. At the present time, however, there are no fluorescent detecting agents satisfying those important factors. Thus the application of fluorescent detecting agents has been limited.

SUMMARY OF THE INVENTION

In view of the above disadvantages of prior fluorescent detecting agents, the present inventors have investigated the compounds having satisfactory properties for practical use as a fluorescent detecting agent and found that the disadvantages of the prior art can be overcome by selection 1,4-dibenzoxazolylnaphthalene or 1,5-diphenyl-3-styrylpyrazoline as a key structure in a strong fluorescent matrix and introducing at least one, desirably more than two alkyl groups of 4 to 8 carbon atoms into phenyl(s) constituting the key structure.

Thus the present invention provides a fluorescent detecting agent comprising a naphthalene compound of formula (I)

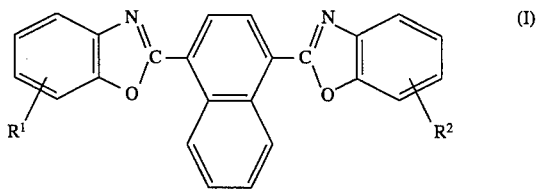

wherein $R^1$ and $R^2$ may be the same or different and each represents an alkyl group of 4 to 8 carbon atoms and/or a pyrazoline compound of formula (II)

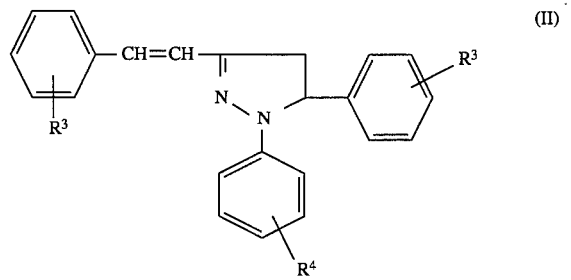

wherein $R^3$ and $R^4$ may be the same or different and each represents hydrogen, an alkoxy group of 1 to 8 carbon atoms or an alkyl group of 4 to 8 carbon atoms, provided that at least one of $R^3$ and $R^4$ represents an alkyl group of 4 to 8 carbon atoms.

DETAILED DESCRIPTION OF THE INVENTION

The fluorescent detecting agents of the present invention are free from color contamination, can provide improved solubility in various solvents, improved compatibility with the materials to be inspected such as resins, improved stability of the dispersion when dispersed in the form of fine particles, improved detecting effect or the like. Among the above improvements, colorless appearance, high solubility in various organic solvents and stability of the dispersion when dispersed in the form of fine particles can be achieved by introducing a higher alkyl group of 4 to 8 carbon atoms as a substituent into the phenyl group. Other substituents such as hydrogen and lower alkyl group cannot achieve such improvements.

The fluorescent detecting agents of the present invention absorb UV light at a wave range centering in 370–390 nm very close to a visible light range and exhibit a strong emission centering in 450–480 nm shifted to a considerably longer wavelength than a conventional fluorescent brightener. Thus they meet necessary requirements for the visual inspection or automatic optical inspection wherein a high-speed, sensitive detecting effect is required.

Further, the fluorescent detecting agents of the present invention can assist a screening effect of the UV-screening agent frequently used in the field of photoresist to increase remarkably the screening effect and also the strong fluorescent emission shifted to a longer wavelength can achieve more accurate and efficient inspection of the circuit pattern.

The UV absorber and UV-screening agent added to an epoxy varnish in the manufacture of a circuit board, e.g., a glass epoxy laminate can well screen UV light centering in about 330–350 nm, but cannot screen UV light at 380–400 nm very close to a visible light range. The fluorescent detecting agents of the present invention have the property of strongly absorbing UV light of the longer wavelength close to the visible light range. Thus the use of the present fluorescent detecting agents in combination with the UV absorber and UV-screening agent can assist more effectively an absorption at the absorption range which cannot be covered by the UV absorber and UV-screening agent alone.

In general, a solder resist film is formed on a conductor pattern layer in the outmost layer of a printed circuit laminate in order to prevent a solder bridge between the conductors upon soldering and to permanently protect the conductor pattern. In the formation of the solder resist using a photoresist through a negative or positive mask, it is usual that the circuit laminate is subjected to a double-side simultaneous exposure by UV light from the viewpoint of economy and operating efficiency. However, the simultaneous exposure will arise an unfavorable event that the desired accuracy of the solder resist is not obtained and the removal of the solder resist is inhibited upon development, since upon exposure UV light transmits the photoresist and then the circuit laminate which results in exposing even each photoresist at the opposite side. To alleviate the unfavorable event, it is essential to use the UV absorber and UV-screening agent.

The inspection of the conductor pattern can be identified in better accuracy and higher sensitivity by utilizing a strong fluorescent emission at a longer wavelength range (450–480 nm). In practice, however, the conductor pattern is identified as a reverse pattern, i.e. a negative image by receiving a fluorescent emission from not the conductor pattern (e.g. copper foil pattern), but from the areas other than the copper foil pattern.

With the improvement in accuracy of recent photosolder resists, higher sensitive resists have been developed and there is desired a laminate having both the property of screening a light of a longer wavelength range (about 400–420 nm) and the property of exhibiting a fluorescent emission of a longer wavelength range (450–480 nm). The above requirements for the laminate can be met by the fluorescent detecting agents of the present invention having a high absorptive power at a longer wavelength range and a high fluorescent emission power at a longer wavelength range.

Accordingly, the compounds of the present invention can be applied as an excellent fluorescent detecting agent response to high accuracy and high efficiency increasingly required in a variety of fields, eventually contributing to a great improvement in productivity.

the compounds of formulas (I) and (II) used as detecting agents in the present invention can be prepared in the known manner. The compound of formula (I) can be prepared for example by reacting (condensation, ring closure) a 1,4-naphthalenedicarboxylic acid, the ester of acid halide thereof with the corresponding o-aminophenols in the presence of a catalyst such as boric acid, zinc chloride. The compound of formula (II) can be readily prepared by reacting the corresponding dibenzalacetones with the corresponding hydrazines in an organic solvent such as alcohol, acetic acid.

Representatives examples of the present compounds are recited below.

Compounds of formula (I):
1,4-bis(5-tert-octylbenzoxazole-2-yl)-naphthalene,
1,4-bis(5-tert-butylbenzoxazole-2-yl)-naphthalene,
1-(5-tert-butylbenzoxazole-2-yl)-4-(5-tert-octylbenzoxazole-2-yl)-4-naphthalene,
1,4-bis(5-n-butylbenzoxazole-2-yl)-naphthalene,
1,4-bis(5-n-pentylbenzoxazole-2-yl)-naphthalene,
1,4-bis(5-n-hexylbenzoxazole-2-yl)-naphthalene,
1,4-bis(5-n-heptylbenzoxazole-2-yl)-naphthalene,
1,4-bis(5-n-octylbenzoxazole-2-yl)-naphthalene,
1,4-bis(6-tert-butylbenzoxazole-2-yl)-naphthalene,
1-(5-n-butylbenzoxazole-2-yl)-4-(5-n-hexylbenzoxazole-2-yl)-4-naphthalene,
1-(5-n-pentylbenzoxazole-2-yl)-4-(5-n-heptylbenzoxazole-2-yl)-4-naphthalene.
1-(5-n-hexylbenzoxazole-2-yl)-4-(5-n-octylbenzoxazole-2-yl)-4-naphthalene.

Compounds of formula (II):
1-phenyl-3-(4-tert-butylstyryl)-5-(4-tert-butylphenyl)pyrazoline.
1-(4-methoxyphenyl)-3-(4-tert-butylstyryl)-5-(4-tert-butylphenyl)pyrazoline,
1(4-tert-butylphenyl)-3-styryl-5-phenylpyrazoline
1-(4-tert-butylphenyl)-3-(4-tert-butylstyryl)-5-(4-tert-butylphenyl)pyrazoline,
1-(4-tert-octylphenyl)-3-styryl-5-phenylpyrazoline,
1-(4-tert-octylphenyl)-3-(4-tert-butylstyryl)-5-(4-tert-butylphenyl)pyrazoline,
1-phenyl-3-(4-n-butylstyryl)-5-(4-n-butylphenyl)pyrazoline,
1(4-n-butylphenyl-3-styryl-5-phenyl)pyrazoline,
1(4-sec-butylphenyl)-3-(4-n-butylstyryl)-5-(4-n-butylphenyl)pyrazoline,
1-(4-ethoxyphenyl)-3-)4-tert-butylstyryl)-5-(4-tert-butylphenyl)pyrazoline,
1-(4-n-propoxyphenyl)-3-(4-tert-butylstyryl)-5-(4-tert-butylphenyl)pyrazoline,
1-(4-n-butoxyphenyl)-3-(4-tert-butylstyryl)-5-(4-tert-butylphenyl)pyrazoline,
1-(4-n-octylphenyl)-3-(4-tert-octylstyryl)-5-(4-tert-octylphenyl)pyrazoline,
1-()4-n-hexylphenyl)-3-(4-n-hexyloxystyryl)-5-(4-n-hexyloxyphenyl)pyrazoline,
1-(4-n-heptylphenyl)-3-(4-n-pentyloxystyryl)-5-(4-n-pentyloxyphenyl)pyrazoline,
1-(4-n-octyloxyphenyl)-3-(4-n-hexylstyryl)-5-(4-n-hexylphenyl)pyrazoline,
1-(4-n-hexylphenyl)-3-styryl-5-phenylpyrazoline,
1-phenyl-3-(4-n-hexylstyryl)-5-(4-n-hexylphenyl)pyrazoline.

Those compounds may be used alone or in combination with two or more compounds. Further, they can be used in combination with other detecting agents and any ultraviolet light screening materials.

The invention is further illustrated by the following examples in which parts are by weight unless otherwise started.

EXAMPLE 1

As a silane coupling agent, 1.0 part of γ-mercaptopropyltrimethoxysilane (KBM803, Shinetsu Chemical Industry Co. Ltd.) and 1.2 part of N-β(aminoethyl)γ-aminopropyltriethoxysilane (KBE603, Shinetsu Chemical Industry Co. Ltd.) were added to 97 parts of ethyl acetate, mixed with stirring and dissolved to form a solution. To the solution was added 0.8 part of 1,4-bis(5-tert-octylbenzoxazole-2-yl)-naphthalene as a fluorescent detecting agent, mixed with stirring and dissolved to prepare a primer composition. The primer composition was coated on a stainless steel sheet and dried to form a coat. The coated sheet was exposed to UV-light having a dominant wavelength of 370 nm, upon which a strong fluorescence have a dominant wavelength of 455 nm was emitted. This fluorescent emission could definitely identify a thickly coated area, thinly coated area, a blurred area and an uncoated area in the primer.

REFERENCE EXAMPLE 1

The appearance and solubility in typical solvents of 1,4-bis(5-tert-octylbenzoxazole-2-yl)-naphthalene (Compound A) and 1,4-bis(benzoxazole-2-yl)-naphthalene (Compound B) were evaluated with the following results.

|  | Appearance | MEK | ethyl acetate | chlorobenzene | xylene | styrene |
|---|---|---|---|---|---|---|
| Compound A | white | 1.0 | 1.3 | 10.2 | 7.6 | 8.8 |
| Compound B | yellow | 0.1 | 0.1 | 0.9 | 0.7 | 1.1 |

Amount of the compound dissolved in 100g of the following solvents

EXAMPLE 2

1.0 part of a mixture comprising 25% of 1,4-bis(5-tert-octylbenzoxazole- 2-yl)-naphthalene, 50% of 1-(5-tert-butylbenzoxazole-2-yl)-4-(5-tert-octylbenzoxazole-2-yl)-naphthalene and 25% of 1,4-bis)(5-tert-butylbenzoxazole-2-yl)-naphthalene as a fluorescent detecting agent was added to a mixture comprising 80 parts of 1,1,2,2-tetrachloro-1,2-difluoroethane, 10 parts of tricresyl phosphate and 10 parts of methylene chloride to prepare a flourescent penetrant.

The performance test was carried out in the following manner. A test piece was prepared by heating the middle of an aluminum sheet at about 500° C. with a burner and quenching its surface with a cold water to cause cracks thereon. The test piece was coated with the fluorescent penetrant of the present invention using a brush and allowed to stand for 10 minutes for drying. The dried test piece was wiped with a dry cloth and excess penetrant was wiped off using a cloth soaked in a detergent (trade name, SUPER GLOW R-II, Marktec Co., Ltd.). The coated test piece was developed by spraying a developer (trade name, SUPER GLOW DN-600S, Marktec Co. Ltd.). The test piece was visually observed in dark place under ultraviolet radiation, by which a defect-indicating pattern of good clearness could be found.

EXAMPLE 3

450 parts of 1-phenyl-3-(4-tert-butylstyryl)-5-(4-tert-butylphenyl)pyrazoline, 18 parts of Emalgen A-500 (trade name, Kao Co. Ltd., Japan(, 20 parts of Demol EP (trade name, Kao Co. Ltd.) and 1012 parts of deionized water were milled with a Dyno-Mill dispersion mill (Willy A. Bachofen AG. Maschinenfabrik Co. Ltd., Switzerland) to particles having a particle diameter of about 2 µm or less. Then 750 parts of a protective colloid, Acquatoto No. 35201 (trade name, Toto Resin Co. Ltd., Japan) were added to make up 3000 parts in total, thus giving a dispersion composition of the fluorescent detecting agent. After storage of the dispersion composition at room temperature for six months, secondary aggregation of the particles and destruction of the dispersion were not observed, but a slight settling was observed sat the bottom of a vessel, which was restored with a slight shaking to an original state. Further, the dispersion composition can be diluted with water in any proportion, with excellent stability.

The dispersion composition is applied to a silane treated glass cloth or glass nonwoven fabric and used in the manufacture of a glass epoxy laminate substrate.

REFERENCE EXAMPLE 2

A comparative dispersion was prepared by the same procedure as mentioned in Example 3, but using 1-( 4-methylphenyl)-3-styryl-5-phenylpyrazoline in place of 1-phenyl-3-(4-tert-butylstyryl)-5-(4-tert-butylphenyl)pyrazoline.

The comparative dispersion and the present dispersion of Example 3 were compared after storage for six months. No change was observed in the dispersion of Example 3. A clear settling was observed in the dispersion of Reference Example 2. Further, redispersion by shaking was impossible, the particle size was increased and the whole dispersion system was heterogeneous. Thus it was impossible to measure accurately the particle size of the comparative dispersion. Microscopic examination indicated that the dispersion particles mostly grew to the size between several ten micrometers and several hundred micrometers and those of 2 µm or less are very few.

EXAMPLE 4

To an epoxy resin was added 0.8% of 1,3-diphenyl-5-(4-tert-butylphenyl)pyrazoline as a ultraviolet light screening agent and 0.2% of 1-phenyl-3-(4-tert-butylstyryl)-5-(4-tert-butylphenyl)pyrazoline as a fluorescent detecting agent to prepare an epoxy varnish. A glass cloth of 0.2 mm thickness was impregnated with the epoxy varnish to prepare a prepreg. Six prepregs were used, a copper foil of 18 µm thickness was laminated on the opposite sides of the prepreg and pressed under heat to provide a copper-clad laminate of the prescribed thickness. The laminate was subjected to coating with a resist, application of a reference pattern, development and etching to prepare a circuit board. The circuit board was subjected to a comparative examination with the reference pattern under UV-light radiation. The maximum absorption wavelength of the fluorescent detecting agent was 386.0 nm which well meets a radiation wavelength in the AOI system. Further, there was obtained a strong fluorescent reflection having a dominant wavelength of 478.2 nm. This wavelength is in good agreement with a wavelength response to a receiving light of a detector and the inspection result was obtained with good sensitivity.

We claim:

1. In a method for optically or visually inspecting a material for surface defects with a fluorescent detecting agent, the improvement comprising using as said fluorescent detecting agent an agent comprising at least one compound selected form the group consisting of a naphthalene compound of formula (I) and a pyrazoline compound of formula (II)

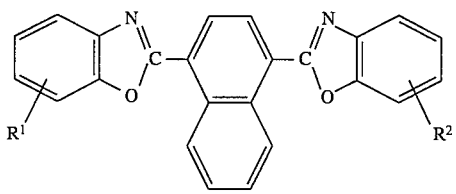

wherein $R^1$ and $R^2$ may be the same or different and each represents an alkyl group of 4 to 8 carbon atoms,

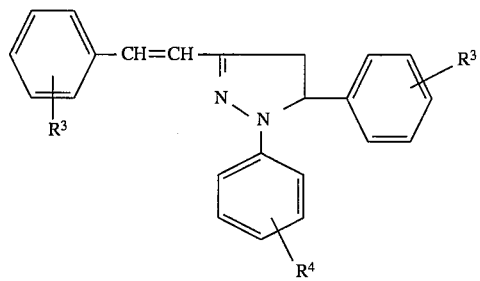

wherein $R^3$ and $R^4$ may be the same or different and each represents hydrogen, an alkoxy group of 1 to 8 carbon atoms or an alkyl group of 4 to 8 carbon atoms, provided that at least one of $R^3$ and $R^4$ represents an alkyl group of 4 to 8 carbon atoms.

2. In a method for optically or visually inspecting a material for surface defects with a fluorescent detecting agent, the improvement comprising using as said fluorescent detecting agent an agent comprising at least one naphthalene compound of formula (I)

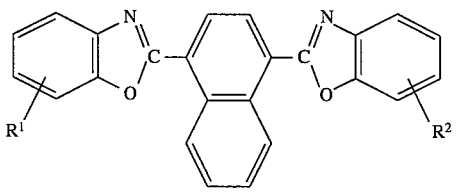

wherein $R^1$ and $R^2$ may be the same or different and each represents an alkyl group of 4 to 8 carbon atoms.

3. In a method for optically or visually inspecting a material for surface defects with a fluorescent detecting agent, the improvement comprising using as said fluorescent detecting agent an agent comprising at least one pyrazoline compound of formula (II)

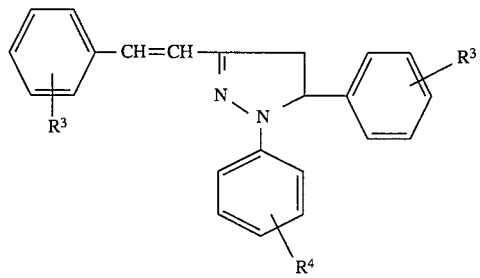

wherein $R^3$ and $R^4$ may be the same or different and each represents hydrogen, an alkoxy group of 1 to 8 carbon atoms or an alkyl group of 4 to 8 carbon atoms, provided that at least one of $R^3$ and $R^4$ represents an alkyl group of 4 to 8 carbon atoms.

4. In a method for optically or visually inspecting an applied pattern or finished circuit in the field of photoresists with a fluorescent detecting agent, the improvement comprising using as said fluorescent detecting agent an agent comprising at least one compound selected from the group consisting of a naphthalene compound of formula (I) and a pyrazoline compound of formula (II)

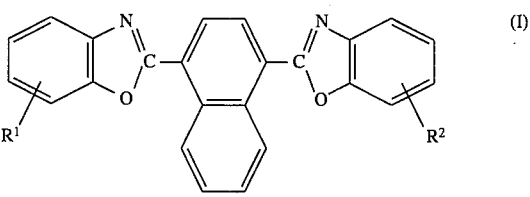

wherein $R^1$ and $R^2$ may be the same or different and each represents an alkyl group of 4 to 8 carbon atoms,

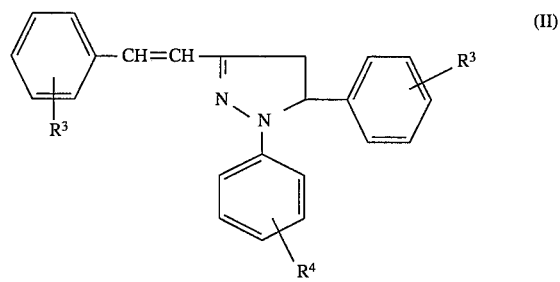

wherein $R^3$ and $R^4$ may be the same or different and each represents hydrogen, an alkoxy group of 1 to 8 carbon atoms or an alkyl group of 4 to 8 carbon atoms, provided that at least one of $R^3$ and $R^4$ represents an alkyl group of 4 to 8 carbon atoms.

5. The method according to claim 4, wherein the fluorescent detecting agent is used in combination with a UV-screening agent.

6. The method of claim 4, wherein at least one compound of said formula (I) is used.

7. The method of claim 4, wherein at least one compound of said formula (II) is used.

* * * * *